(12) United States Patent
Morgan (10) Patent No.: US 11,849,985 B2
(45) Date of Patent: Dec. 26, 2023

(54) TISSUE SCREW AND METHOD OF MAKING AND USING SAME

(71) Applicant: ConneX BioMedical, Inc., Breckenridge, CO (US)

(72) Inventor: Jeremy H. Morgan, Missoula, MT (US)

(73) Assignee: ConneX BioMedical, Inc., Aurora, CO (US)

( * ) Notice: Subject to any disclaimer, the term of this patent is extended or adjusted under 35 U.S.C. 154(b) by 78 days.

(21) Appl. No.: 17/458,297

(22) Filed: Aug. 26, 2021

(65) Prior Publication Data

US 2023/0060272 A1  Mar. 2, 2023

(51) Int. Cl.
*A61B 17/86* (2006.01)

(52) U.S. Cl.
CPC ........ *A61B 17/869* (2013.01); *A61B 17/8615* (2013.01); *A61B 17/8625* (2013.01)

(58) Field of Classification Search
CPC .................................................. A61B 17/869
See application file for complete search history.

(56) References Cited

U.S. PATENT DOCUMENTS

2008/0097444 A1* 4/2008 Erickson ............ A61B 17/8052
606/281

* cited by examiner

*Primary Examiner* — Olivia C Chang
(74) *Attorney, Agent, or Firm* — David G. Rosenbaum; Rosenbaum IP, P.C.

(57) ABSTRACT

A monolithic tissue screw fabricated of a single, unitary piece of material. The monolithic tissue screw has a helical coil portion and screw head portion with a driver aperture passing axially through the screw head portion and a co-axial with the helical coil portion such that a rotational torsional force applied by a mating driver to the driver aperture causes the helical coil portion to rotate about its axis. The helical coil portion engages tissue and draws the helical coil and the screw head portion into the tissue substantially only with the application of the rotational torsional force and substantially without an axial force applied to the tissue screw.

32 Claims, 13 Drawing Sheets

TISSUE SCREW AND METHOD OF MAKING AND USING SAME

BACKGROUND OF THE INVENTION

The present disclosure relates generally to tissue screws, methods of making same, and methods of using same. More particularly, the present disclosure pertains to a monolithic tissue screw fabricated of a single, unitary piece of material. Still more particularly, the present disclosure pertains to a monolithic tissue screw having a helical coil portion and a screw head portion with a driver aperture passing axially through the screw head portion and co-axial with the helical coil portion.

Tissue screws typically are either of unitary or two piece construction in which the tissue screw head has a blind recess or a shaped head configured to couple to a driver and a screw shank having external threads projecting radially outward from the screw shank. In either case, it is necessary to apply an axial force to the tissue screw while also applying a rotational to the tissue screw to drive the screw into the desired tissue. Helical coils are also know for use in joining to soft tissue, such as for affixing pacemaker leads (See, e.g., US20180085571A1 or affixing surgical mesh to soft tissue in hernia repair (See, e.g., US20030009441A; such helical coils, however, typically do not have screw heads that engage with a driver to join the helical coil to the soft tissue.

The tissue screw of the present disclosure is configured to be driven into tissue based substantially only upon rotational force applied by the driver to the driver aperture and substantially without axial force applied to the coil portion of the tissue screw. The driver aperture is configured to allow a driver to pass into and through the driver aperture and apply a torsional force to the tissue screw head portion and rotate the helical coil portion, causing a tapered distal end of the helical coil portion to engage with tissue and allow the coil to draw down over the driver and into the tissue substantially only with the application of rotational force to the tissue head portion. In this manner, the driver acts to apply the rotational torque to the tissue screw and be axial guidance for the tissue screw as it is drawn into the tissue by rotation of the helical coil portion.

SUMMARY OF THE INVENTION

It is an object of the present disclosure to provide a monolithic tissue screw having a unitary structure including a tissue screw head portion and a helical coil portion.

It is a further object of the present disclosure to provide a monolithic tissue screw in which the tissue screw head portion and the helical coil portion are fabricated from a single, unitary piece of precursor material.

It is yet a further object of the present disclosure to provide a monolithic tissue screw in which the tissue screw head portion has a driver aperture passing into and through the tissue screw head portion along a central longitudinal axis of the monolithic tissue screw.

It is still another objective of the present disclosure to provide a monolithic tissue crew in which the driver aperture is configured to accept a driver within the driver aperture such that the driver passes into and through the driver aperture along the central longitudinal axis of the monolithic tissue screw.

System and method of synchronously driving two or more tissue screws into and through the sewing skirt of an apical cuff, axially securing one or more compression plates and/or rings to bear against the sewing skirt, and affix the apical cuff to heart tissue.

It is another object of the present disclosure to provide a system and method of synchronously driving two or more tissue screws at the same rate and torque to axially secure an apical cuff to heart tissue.

It is a further object of the present disclosure to provide a system and method of synchronously driving two or more tissue screws with little or no axial force applied to the tissue screws.

It is yet another object of the present disclosure to provide a system and method of targeting a desired position for affixing an apical cuff to heart tissue.

It is still another object of the present disclosure to provide a monolithic tissue screw in which the helical coil portion defines an on open region within the helical coil that receives the driver within the open region.

It is still yet another object of the present disclosure to provide a monolithic tissue screw in which the helical coil portion has a tapered distal end.

It is yet a further object of the present disclosure to provide a monolithic tissue screw in which the helical coil portion has a continuous pitch to helical windings of the helical coil portion.

It is still another further object of the present disclosure to provide a monolithic tissue screw in which the helical coil portion has more than one pitch to the helical windings of the helical coil portion.

It is still further object of the present disclosure to provide a monolithic tissue screw in which the helical portion includes a helical winding having a transverse cross-sectional shape that is selected from the group of polygonal, circular, ovular, or elliptical.

It is another further object of the present disclosure that the driver for the monolithic tissue screw apply a torsional force to tissue screw head portion by engaging with lateral wall surfaces of the driver aperture substantially without axial force being applied to the helical coil portion or the tissue screw head portion.

These and other objects, features and advantages of the disclosed synchronous drive system and its sub-systems will be more apparent to those of ordinary skill in the art from the following more detailed description of the preferred embodiments of the present disclosure taken with reference to the accompanying Figures, individually and collectively. In the accompanying Figures, like structure and/or functional features are identified by like reference numerals for ease of reference.

DETAILED DESCRIPTION OF THE PREFERRED EMBODIMENTS

The devices, system and methods of the present disclosure will be described with reference to certain exemplary embodiments thereof. These exemplary embodiments are intended to be illustrative and non-limiting examples of the present invention. The example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. Those of ordinary skill in the art will understand and appreciate that variations in materials, structure, material properties, and tolerances may be made without departing from the scope of the invention, which is defined only by the claims appended hereto and their range of equivalents. In some example embodiments, well-known processes, well-known device structures, and well-known technologies are not described in detail.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, and C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching when used throughout the figures to denote different parts but not necessarily to denote the same or different materials.

For ease of understanding, the present invention is described with reference to the accompanying Figures. In the accompanying Figures like elements are identified by like reference numerals.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

"Substantially" is intended to mean a quantity, property, or value that is present to a great or significant extent and less than totally.

"About" is intended to mean a quantity, property, or value that is present at ±10%. Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

The steps recited in any of the method or process descriptions may be executed in any order and are not necessarily limited to the order presented. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods, and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Turning to FIGS. 1-4 a first variant of the tissue screw 10 of the present invention is depicted. Tissue screw 10 consists generally of a tissue screw head portion 12 and an open helical coil portion 14. The tissue screw head portion 12 and the open helical coil portion 14 are integrally and monolithically fabricated from a single, unitary piece of material and are contiguous with one and other without joints, couplings, adhesives, welds, or the like. The open helical coil portion 14 has plural helical windings and extends from a proximal aspect 15 thereof to a distal aspect 19 thereof. The proximal aspect 15 of the open helical coil portion 14 extends from a lower surface of the tissue screw head portion 12 and the plural helical windings circumscribe and define a central open space 17 within the open helical coil portion 14.

The open helical coil portion 14 terminates at the distal aspect 19 thereof in a tapered distal end 20 configured to penetrate into tissue.

The tissue screw head portion 12 includes a driver aperture 16 that passes axially into and through the tissue screw head portion 12 and communicate with the central open space 17. The driver aperture 16 may be any desired shape, including, without limitation, polygonal, ovular, elliptical or other shape suitable for engaging a mating driver. A mating driver (not shown) passes into and through the driver aperture 16 and into the central open space 17 circumscribed by the open helical coil portion 14. The driver aperture 16 has side walls that act both as load bearing surfaces against which the mating driver bears when a torsional rotational force is applied by the mating driver to the driver aperture 16 and guide surfaces as the tissue screw 10 moves axially along a length of the driver.

Alternative configurations of the tissue screw head portion 12 are also contemplated by the present disclosure. For example, the driver aperture 16 may be configured to accommodate a guidance shaft to guide axial movement of the tissue screw 10 along a length of the driver while the rotational force is provided by a driver interfacing either circumferentially about a shaped perimeter of the tissue screw head portion or by a pin and opening or pin and slot arrangement where additional driver apertures 16 are positioned in a radially offset manner from the central longitudinal axis of the tissue screw 10 and the driver has a pin or other engaging protrusion that engages with the driver apertures 16 to rotate the tissue screw head portion 12. In this alternative configuration, the rotational force applied to the tissue screw head portion 12 is provided by the driver and the axial guidance is provided by a shaft or other similar structure passing through the driver aperture 16.

A clocking marker 21 may be provided either on or in the tissue screw head portion 12 or in association with the driver aperture 16. Where provided in association with the driver aperture 16, clocking marker 21 may be contiguous with the driver aperture 16 and extend into the tissue screw head portion 12 from the wall of the driver aperture 16, as illustrated, or may be a projection from the tissue screw head portion 12 and into the driver aperture 16. Clocking marker 21, where optionally provided, serves to provide the user with a visual indicia of the rotational position of the tissue screw 10. Clocking marker 21 is preferably in axial alignment with the tapered distal end 20 of the open helical coil portion 14 so that the user has a visual indictor of the rotational position of the tapered distal end 20.

Figure 6:
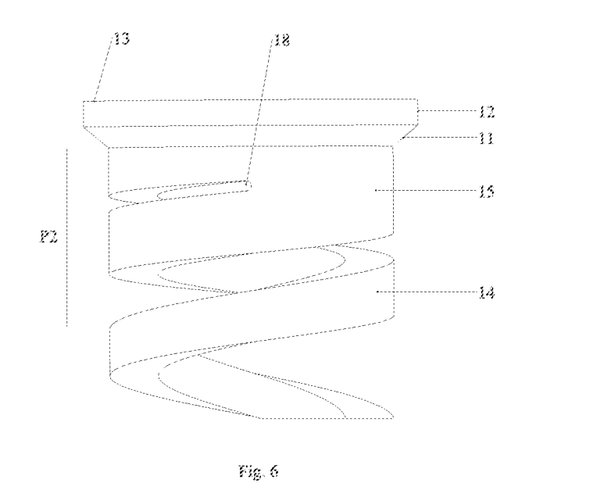
FIG. 6 is an enlarged sectional view of a tissue head screw section and proximal helical coil section in accordance with the present disclosure.
Figure 11:
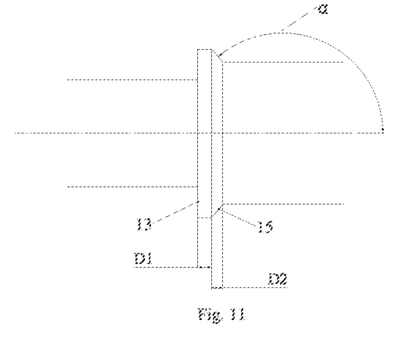
FIG. 11 is a fragmentary side elevational view of a tissue screw head section prior to forming the helical coil section and removing the stem.

As illustrated in FIGS. 6 and 11, tissue screw head portion 12 has a substantially planar surface 13 at its proximal end, and a tapered section 11 that extends distally from the substantially planar surface 13 and tapers toward a central axis of the tissue screw 10. The tapered section 11 has a taper angle α that may be configured to mate with a tapered recess such that the substantially planar surface 13 is co-planar with a surface that the tapered recess is within. Taper angle α may be between, about 20 degrees and 90 degrees relative to the longitudinal axis of the tissue screw 10. Tapered section 11 may have a linear taper or a curved profile taper to allow some degree of angular movement of the tissue screw 20 from perpendicular.

Upon applying a torsional rotational force from the driver to the driver aperture 16, the open helical coil portion 14 will begin to rotate about its longitudinal axis and the tapered distal end 20 of the open helical coil portion 14 will penetrate into tissue. As the torsional rotational force continues to be applied, the open helical coil portion 14 will be drawn down into the tissue under the influence substantially only of the rotation of the open helical coil portion 14 and substantially without an axial force being applied to the tissue screw 10.

Figure 7:
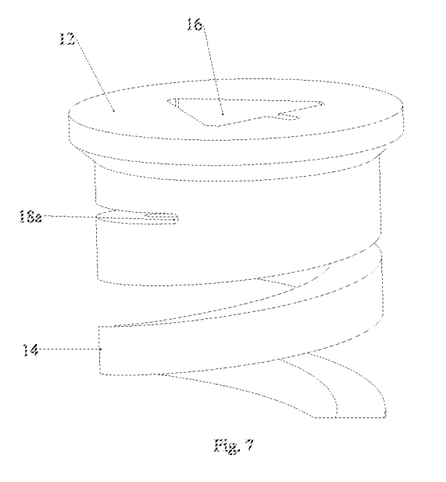
FIG. 7 is an enlarged sectional view of a tissue head screw section and proximal helical coil section in accordance with a third variant of the present disclosure.
Figure 8:
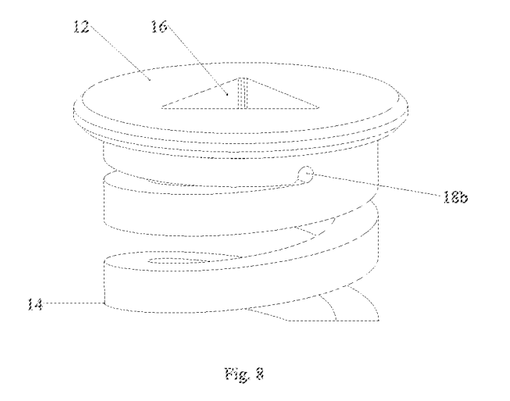
FIG. 8 is an enlarged sectional view of a tissue head screw section and proximal helical coil section in accordance with a fourth variant of the present disclosure.

It will be understood by those skilled in the art that transfer of force from the driver to the tissue screw head portion 12 imparts a rotational force to the open helical coil portion 14. This rotational force imparts a focal strain at a junction 18 between the tissue screw head portion 12 and the open helical coil portion 14. In order to disburse the focal strain at the junction 18, the junction 18 may be configured as a taper 18a (FIG. 7) between the most proximal helical winding of the open helical coil portion 14 and the most distal aspect of the tissue screw head portion 12. A strain relief feature 18b (FIG. 8) may also be included, such as an enlarged open region communicating with a tapered slot at the most proximal helical winding of the open helical coil and the most distal aspect of the tissue screw head portion 12.

Figure 1:
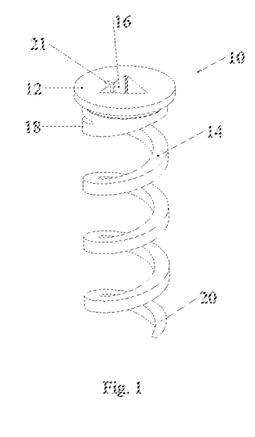
FIG. 1 is a perspective view of a first variant of tissue screw in accordance with the present disclosure.
Figure 2:
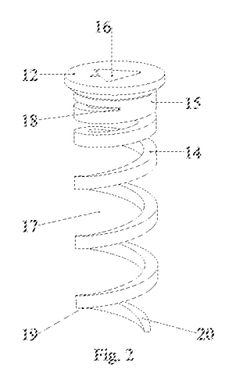
FIG. 2 is a side elevational view of the first variant of the tissue screw in accordance with the present disclosure
Figure 3:
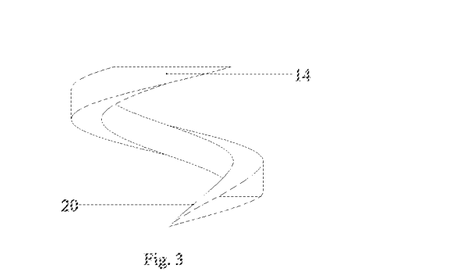
FIG. 3 is an enlarged sectional view of a tapered distal end of the first variant of the tissue screw in accordance with the present disclosure.
Figure 4:
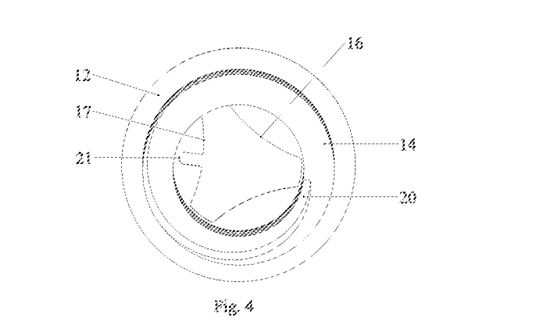
FIG. 4 is an end elevational view of the first variant of the tissue screw in accordance with the present disclosure.
Figure 5:
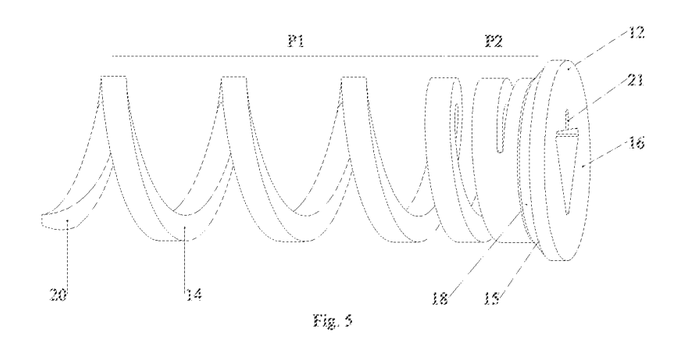
FIG. 5 a side elevational view of a second variant of the tissue screw in accordance with the present disclosure.

The open helical coil portion 14 has plural helical windings. The plural helical windings have a pitch between adjacent windings that corresponds to a distance of one complete helix turn, i.e., 360 degree arc, and is measured parallel to the axis of the helix. The tissue screw 10 may have an equal helical pitch along its entire length, may have a gradient pitch, or it may have two or more different pitches along its entire length. FIGS. 5 and 6 illustrate a second variant of the tissue screw 10 in which the open helical coil portion 14 has a first pitch P1 and a second pitch P2, with the first helical pitch P1 present relatively distally on the open helical coil portion 14 and the second helical pitch P2 present relatively proximally on the open helical coil portion 14. As illustrated first helical pitch P1 is relatively greater than second helical pitch P2. It will be understood and appreciated by those skilled in the art that more than two different helical pitches may be employed and that the arrangement of the different helical pitches may be varied along the length of the open helical coil portion 14. For example, a helical pitch gradient may be employed in which a first helical pitch at a proximal end of the open helical coil portion 14 may be relatively smaller, a second distally adjacent helical pitch may be relatively larger than the first helical pitch, and a third again distally adjacent helical pitch may be relative larger than both the first and second helical pitches. Further, for example, the diameter of the open helical coil portion 14 as well as the helical pitch may also be varied such that the diameter of successive helical windings may either increase or decrease along the length of the open helical coil portion 14. Where the diameter of successive helical windings increases along the length of the open helical coil portion 14, the most distal helical winding will have a larger diameter than the most proximal helical winding. Conversely, where the diameter of successive helical windings decreases along the length of the open helical coil portion 14, the most distal helical winding will have a smaller diameter than the most proximal helical winding.

Figure 9:
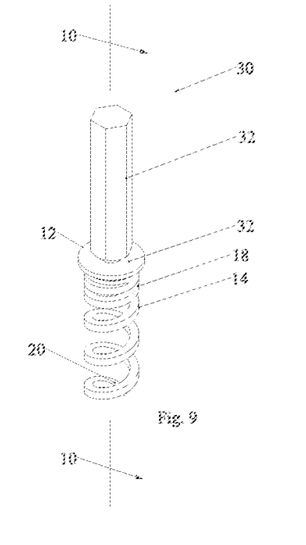
FIG. 9 is a perspective view of a fifth variant of a monolithic tissue screw and driver assembly in accordance with the present disclosure.
Figure 10:
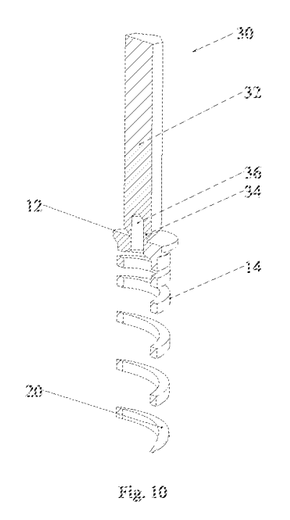
FIG. 10 is a perspective cross-sectional view taken along line 9-9 of FIG. 8.

A third variant of the tissue screw 30 illustrated in FIGS. 9 and 10 is also provided in which the tissue screw head portion 12 does not have a driver aperture 16, but rather has an integral, monolithic driver 32 that extends proximally from the tissue screw head portion 12 with a frangible section 34 at the junction between the tissue screw head portion 12 and the monolithic driver 32. The frangible section 34 is configured to detach from the tissue screw head portion 12 at a predetermined torque setting. Detachment of the frangible section 34 from the tissue screw head portion 12 prevents over-torquing the tissue screw 30 and potentially damaging either the tissue, device, implant, or other thing being joined to the tissue. The frangible section 24 may consist of a diametrically narrowed distal section of the integral, monolithic driver 32 as illustrated in FIG. 10. Alternatively frangible section 24 may be a weakened section of the material of integral, monolithic driver 32. Optionally, a blind bore 36 may be provided that passes proximally through the tissue screw head portion 12 and into a distal region of the integral, monolithic driver 32. Blind bore 36 facilitates the further weakening of the frangible section 34 by creating even thinner wall thicknesses of the monolithic driver 32 at the frangible section 34. Further, where the blind bore 36 is provided, the blind bore 36 may have a transverse cross-sectional shape configured to mate with a separate driver to fine tune the rotational position of the tissue screw 30 after the driver integral, monolithic driver 32 has been removed from the tissue screw head portion 12 at the frangible section 36.

Figure 12:
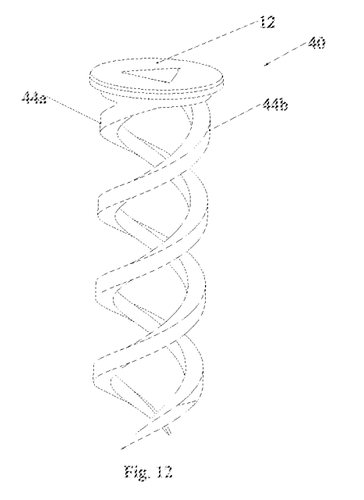
FIG. 12 is a perspective view of a sixth variant of the monolithic tissue screw in accordance with the present disclosure.
Figure 13:
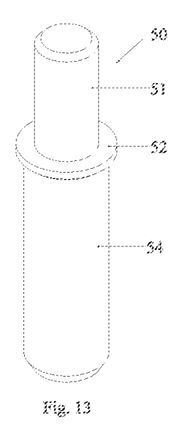
FIG. 13 is perspective view of a precursor blank for forming the variants of the monolithic tissue screw in accordance with the present invention.
Figure 14:
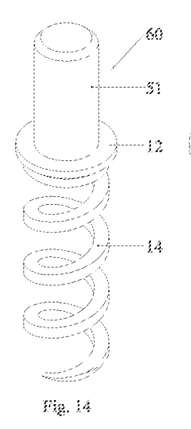
FIG. 14 is a perspective view of the precursor blank with the helical coil section formed in accordance with the present invention.
Figure 15:
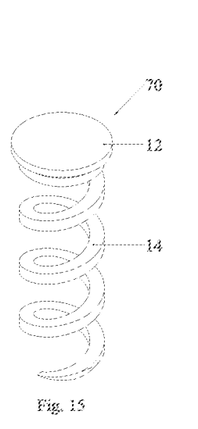
FIG. 15 is a perspective view of the tissue screw head section after removal of the stem in accordance with the present invention
Figure 16:
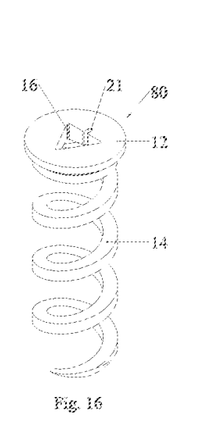
FIG. 16 is a perspective of the formed tissue screw in accordance with a variant of the present disclosure.

A further variant of the tissue screw 40 is illustrated in FIG. 12. Tissue screw 40 is similar to tissue screw 10, and/or 30, except that at least two open helical portions 44a, 44b project from the tissue screw head portion 12. Open helical portions 44a, 44b, like open helical coil portion 14, may have a constant helical pitch or a variable helical pitch, and, also like open helical coil portion 14, may have different diameters of helical windings along the longitudinal length of the at least two open helical portions 44a, 44b. Open helical portions 44a, 44b are offset from each other about the circumference of the tissue screw 40, and may be offset less than or equal to 180 degrees from each other. It is important that the at least two open helical portions 44a, 44b having the same helical orientation, i.e., either clockwise or counterclockwise, to ensure that the tissue screw 40 will thread into and out of the tissue to which it is applied with the at least two open helical portions 44a, 44b penetrating into the tissue simultaneously. Also like tissue screw 10, and/or 30, the tissue screw head portion 12 is integral and monolithic with the at least two open helical portions 44a, 44b, and an junction 18 transitions between the tissue screw head portion 12 and the at least two open helical portions 44a, 44b without joints, couplings, adhesives, welds, or the like.

FIGS. 13-16 illustrate steps in forming the integral and monolithic tissue screws 10, 30, and 40 in accordance with the present invention. First, a cylindrical blank is formed into a tissue screw precursor 50 having a stem 51, a tissue screw head flange 52, and a helical coil blank 54. The tissue screw head flange 52 will have a greater diameter than the helical coil blank 54 which has a greater diameter than the stem 51. The open helical coil portion 14 and the tissue screw head portion 12 are then formed, such as by machining or laser cutting, by removing sections of the helical coil blank 54 to form the helical windings, the tapered distal end 20, and the tapered section 11 of the tissue screw head portion 12, to form the tissue screw precursor 60. The stem 51 is then removed from the tissue screw precursor to form tissue screw blank 70 with substantially planar surface 13 of the tissue screw head portion 12. The driver aperture 16 and optional clocking marker 21 are then formed in the substantially planar surface 13 of the tissue screw head portion 12 to form the tissue screw 80. Tissue screw 80 may then be further processed, such as by heat tempering, polishing, coating, and sterilizing.

Figure 17:
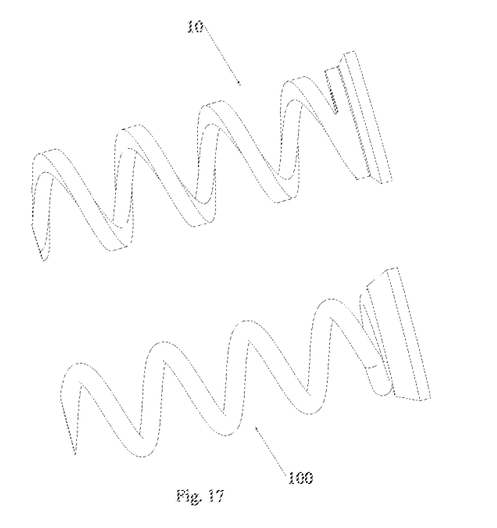
FIG. 17 is perspective views comparing the monolithic tissue screw in accordance with the present disclosure compared to a tissue screw having two piece construction.

FIG. 17 is a photographic comparison between the integral, monolithic tissue screw 10 (and, similarly, tissue screws 30, 40) and a prior tissue screw 100 having a two piece construction where the helical coil is joined to the tissue screw head by welding.

While the present disclosure has been made with reference to the accompanying Figures and exemplary and alternative embodiments or variants of the present invention, it will be understood that the present disclosure is not intended to be limited only to the described elements, embodiments, materials, methods, assemblies, structures, dimensions, geometries or the like. Rather, the scope of the present disclosure is intended to be restricted only by the claims appended hereto. Variations in sizes, shapes, geometries, combinations, assemblies, materials or the like are expressly contemplated by the present disclosure.

What is claimed is:

1. A monolithic tissue screw comprising:
   a. A tissue head section having a driver aperture passing axially through the tissue head section, the driver aperture being configured to receive a driver therethrough co-axial with a central longitudinal axis of the monolithic tissue screw; and
   b. An open helical coil section unitary with the tissue head section and projecting from a lower surface of the tissue head section, the open helical coil section comprises plural helical windings having different pitches and having a tapered distal tip, the open helical coil section defining a central opening configured to allow the driver to pass into the central opening and extend at least a portion of a length of the helical coil section.

2. The monolithic tissue screw according to claim 1, wherein the driver aperture has a polygonal shape defining driver aperture side walls.

3. The monolithic tissue screw according to claim 2, wherein the driver aperture side walls engage with a driver and are configured to transfer torsional force applied by the driver to the tissue head section.

4. The monolithic tissue screw according to claim 1, wherein the helical coil section has a proximal junction with a lower surface of the tissue head section.

5. The monolithic tissue screw according to claim 4, wherein the proximal junction further comprises a strain relief section.

6. The monolithic tissue screw according to claim 5, wherein the strain relief section further comprises an enlarged rounded opening.

7. The monolithic tissue screw according to claim 5, wherein the strain relief section further comprises a tapered opening.

8. The monolithic tissue screw according to claim 1, wherein the helical coil section has a transverse cross-sectional shape selected from the group of polygonal, circular, ovular, and elliptical.

9. The monolithic tissue screw of claim 1, wherein the helical coil section further comprises a second helical coil section offset from the open helical coil section.

10. The monolithic tissue screw of claim 9, wherein the second helical coil section is diametrically offset from the open helical coil section about a circumference of the tissue screw.

11. The monolithic tissue screw of claim 1, wherein the tissue head section further comprises a substantially planar upper surface and a beveled side wall tapering diametrically toward the central longitudinal axis of the tissue screw and contiguous with a proximal end of the open helical coil section.

12. A monolithic tissue screw, comprising:
    a. A tissue head section having a polygonal driver aperture passing axially through the tissue head section, the driver aperture being configured to receive a mating driver therethrough co-axial with a central longitudinal axis of the monolithic tissue screw; and
    b. An open helical coil section unitary with the tissue head section and projecting from a lower surface of the tissue head section, the open helical coil section having a tapered distal tip and defining a central opening configured to allow the driver to pass into the central opening and extend at least a portion of a length of the helical coil section, the open helical coil further comprising plural helical windings having different pitches.

13. The monolithic tissue screw according to claim 12, wherein the open helical coil section is configured to rotate about its axis upon application of substantially only a rotational force applied by the mating driver to the polygonal driver aperture, wherein the driver aperture has a polygonal shape defining driver aperture side walls.

14. The monolithic tissue screw according to claim 12, further comprising a strain relief section at a junction between the tissue screw head section and the open helical coil section.

15. The monolithic tissue screw according to claim 12, wherein the helical coil section has a transverse cross-sectional shape selected from the group of polygonal, circular, ovular, and elliptical.

16. The monolithic tissue screw of claim 12, wherein the helical coil section further comprises a second helical coil section offset from the open helical coil section.

17. The monolithic tissue screw of claim 12, wherein the second helical coil section is diametrically offset from the open helical coil section about a circumference of the tissue screw.

18. A monolithic tissue screw consisting essentially of:
   a. A tissue head section having a driver aperture passing axially through the tissue head section, the driver aperture having a polygonal shape defining driver aperture side walls and being configured to receive a driver therethrough co-axial with a central longitudinal axis of the monolithic tissue screw; and
   b. An open helical coil section unitary and monolithic with the tissue head section and projecting from a lower surface of the tissue head section, the open helical coil section defining a central opening configured to allow the driver to pass into the central opening and extend at least a portion of a length of the helical coil section.

19. The monolithic tissue screw according to claim 18, wherein the driver aperture side walls engage with a driver and are configured to transfer torsional force applied by the driver to the tissue head section.

20. The monolithic tissue screw according to claim 18, wherein the helical coil section has a proximal junction with a lower surface of the tissue head section.

21. The monolithic tissue screw according to claim 20, wherein the proximal junction further comprises a strain relief section.

22. The monolithic tissue screw according to claim 21, wherein the strain relief section further comprises an enlarged rounded opening.

23. The monolithic tissue screw according to claim 21, wherein the strain relief section further comprises a tapered opening.

24. The monolithic tissue screw according to claim 18, wherein the helical coil section has a transverse cross-sectional shape selected from the group of polygonal, circular, ovular, and elliptical.

25. The monolithic tissue screw of claim 18, wherein the helical coil section further comprises a second helical coil section offset from the open helical coil section.

26. The monolithic tissue screw of claim 25, wherein the second helical coil section is diametrically offset from the open helical coil section about a circumference of the tissue screw.

27. The monolithic tissue screw of claim 18, wherein the tissue head section further comprises a substantially planar upper surface and a beveled side wall tapering diametrically toward the central longitudinal axis of the tissue screw and contiguous with a proximal end of the open helical coil section.

28. A monolithic tissue screw, comprising:
   a. A tissue head section having a driver aperture passing axially through the tissue head section, the driver aperture being configured to receive a driver therethrough co-axial with a central longitudinal axis of the monolithic tissue screw;
   b. An open helical coil section unitary and monolithic with the tissue head section and projecting from a lower surface of the tissue head section, the open helical coil section defining a central opening configured to allow the driver to pass into the central opening and extend at least a portion of a length of the helical coil section; and
   c. A strain relief section comprising an enlarged rounded opening at a juncture between the tissue head section and the open helical coil section, the opening passing through a lateral thickness of the juncture.

29. The monolithic tissue screw according to claim 28, wherein the driver aperture has a polygonal shape defining driver aperture side walls configured to engage with a driver and transfer torsional force applied by the driver to the tissue head section and the open helical coil section.

30. The monolithic tissue screw according to claim 28, wherein the strain relief section further comprises a tapered opening.

31. The monolithic tissue screw according to claim 28, wherein the helical coil section has a transverse cross-sectional shape selected from the group of polygonal, circular, ovular, and elliptical.

32. The monolithic tissue screw of claim 28, wherein the helical coil section further comprises a second helical coil section offset from the open helical coil section.

* * * * *